(12) United States Patent
Kim et al.

(10) Patent No.: US 12,365,708 B2
(45) Date of Patent: Jul. 22, 2025

(54) METHOD FOR SOLUBLE EXPRESSION AND PURIFICATION OF HYDROPHOBIN

(71) Applicant: INDUSTRY FOUNDATION OF CHONNAM NATIONAL UNIVERSITY, Gwangju (KR)

(72) Inventors: Geun Joong Kim, Gwangju (KR); Dae Eun Cheong, Gwangju (KR); Ho-Dong Lim, Jeongeup-si (KR); Sang-Oh Ahn, Gwangju (KR); Sung Hwan You, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 125 days.

(21) Appl. No.: 18/056,708

(22) Filed: Nov. 17, 2022

(65) Prior Publication Data
US 2023/0119241 A1 Apr. 20, 2023

Related U.S. Application Data

(62) Division of application No. 16/944,078, filed on Jul. 30, 2020, now abandoned.

(30) Foreign Application Priority Data

May 20, 2020 (KR) ........................ 10-2020-0060264

(51) Int. Cl.
C07K 14/00 (2006.01)
C07K 7/06 (2006.01)
C07K 14/37 (2006.01)

(52) U.S. Cl.
CPC ................ *C07K 14/37* (2013.01); *C07K 7/06* (2013.01); *C07K 2319/00* (2013.01)

(58) Field of Classification Search
CPC ....... C07K 14/37; C07K 7/06; C07K 2319/00
See application file for complete search history.

(56) References Cited

U.S. PATENT DOCUMENTS

2007/0077619 A1* 4/2007 Ostermann .......... C12N 15/815 435/254.2
2015/0057434 A1* 2/2015 Schelle .................. C07K 14/37 568/840

FOREIGN PATENT DOCUMENTS

| KR | 100919704 B1 | 10/2009 | |
| KR | 20140022839 A | 2/2014 | |
| KR | 101446054 B1 | 10/2014 | |
| WO | WO-2005033316 A2 * | 4/2005 | ........... C12N 15/815 |

OTHER PUBLICATIONS

Longobardi et al in "Environmental Conditions Modulate the Switch among Different States of the Hydrophobin Vmh2 from Pleurotus ostreatus" (Biomacromolecules vol. 13, pp. 743-750, published Jan. 31, 2012). (Year: 2012).*
WO2005033316_Score_result_for_instant_SEQ_10. (Year: 2005).*
WO2005033316_Score_result_for_instant_SEQ_2 (Year: 2005).*
WO2005033316_Score_result_for_instant_SEQ_3 (Year: 2005).*
Ahn_et_al_2021 (Year: 2021).*
Linder, M. et al., "Hydrophobins: the protein-amphiphiles of filamentous fungi," FEMS Microbiology Reviews, vol. 29, No. 5, Nov. 2005, 20 pages.
Kwan, A. et al., "Structural basis for rodlet assembly in fungal hydrophobins," Proceedings of the National Academy of Science of the United States of America, vol. 103, No. 10, Mar. 7, 2006, 6 pages.
Wohlleben, W. et al., "Recombinantly produced hydrophobins from fungal analogues as highly surface-active performance proteins," European Biophysics Journal, vol. 39, Mar. 17, 2009, 13 pages.
Bayry, J. et al., "Hydrophobins—Unique Fungal Proteins," PLoS Pathogens, vol. 8, No. 5, May 31, 2012, 4 pages.
Singh, P. et al., "Effect of Signal Peptide on Stability and Folding of *Escherichia coli* Thioredoxin," PLOS ONE, vol. 8 No. 5, May 7, 2013, 14 pages.
Sang-Oh, A. et al., "A Frame Work for Soluble Expression and Easy Purification of Class I Hydrophobin DewA: ATPS using IPA," Proceedings of the 15th KSMB Annual Meeting & Symposium, Nov. 7, 2019, Gangneung-si, Gangwon-do, Korea, 5 pages.
Verma, M. et al., "A short translational ramp determines the efficiency of protein synthesis," Nature Communications, vol. 10, No. 5774, Dec. 18, 2019, 15 pages.
"Dewa_Emeni Spore-Wall Fungal Hydrophobin Dewa Precursor [Aspergillus nidulans FGSC A4]," NCBI Website, Available Online at https://www.ncbi.nlm.nih.gov/protein/XP_681275.1?report=genbank&log$=protalign&blast_rank=1&RID=NB2KF6N3014, Available as Early as Sep. 7, 2020, 2 pages.
Ahn, S. et al., "Soluble Expression and Efficient Purification of Recombinant Class I Hydrophobin DewA," International Journal of Molecular Sciences, vol. 22, No. 15, Jul. 22, 2021, 11 pages.
Korean Intellectual Property Office, Office Action Issued in Application No. 10-2020-0060264, Jun. 19, 2022, 12 pages.

* cited by examiner

*Primary Examiner* — Catherine S Hibbert
(74) *Attorney, Agent, or Firm* — McCoy Russell LLP (57) ABSTRACT

A method of expressing hydrophobin in a soluble form and a method of purifying hydrophobin, and more particularly, to a method of expressing a recombinant fusion protein including hydrophobin in a soluble form in a host cell and then purifying the expressed recombinant fusion protein are provided.

4 Claims, 3 Drawing Sheets
Specification includes a Sequence Listing.

METHOD FOR SOLUBLE EXPRESSION AND PURIFICATION OF HYDROPHOBIN

CROSS-REFERENCE TO RELATED APPLICATIONS

The present application is divisional of U.S. Non-Provisional patent application Ser. No. 16/944,078, entitled "METHOD FOR SOLUBLE EXPRESSION AND PURIFICATION OF HYDROPHOBIN," and filed on Jul. 30, 2020. U.S. Non-Provisional patent application Ser. No. 16/944,078 claims priority to Korean Patent Application No. 10-2020-0060264, filed on May 20, 2020. The entire contents of each of the above-listed applications are hereby incorporated by reference for all purposes.

SEQUENCE LISTING

The instant application contains a Sequence Listing which has been filed electronically in XML format and is hereby incorporated by reference in its entirety. Said XML copy, created on Nov. 16, 2022, is named PLS20312DIV1ST26.xml and is 15 KB in size.

TECHNICAL FIELD

The following disclosure relates to a method of expressing hydrophobin in a soluble form and a method of purifying hydrophobin, and more particularly, to a method of expressing a recombinant fusion protein including hydrophobin in a soluble form in a host cell and then purifying the expressed recombinant fusion protein.

BACKGROUND

Hydrophobin is a small protein initially isolated from *Shizophyllum commune*. The hydrophobin is composed of 100 to 150 amino acids, and is mainly expressed in a mycelia fungus. In hyphae growth of fungi, the hydrophobin which is amphipathic forms a hydrophobic surface layer through self-assembly when a monomer thereof is secreted to the outside. As a result, the hydrophobin acts to coat a surface of the hypha through an amphiphilic polymer composition. Through the above action, the hydrophobin not only enables the hypha to effectively respond to changes in the surrounding environment but also functions as a shield between a cell wall and an air layer or at an interface between a cell wall and a solid surface during sporulation, fruiting body development, and host invasion through infection structure formation (Bayry et al., 2012).

The hydrophobin forms four disulfide bonds in a molecule from eight cysteine residues included in a protein molecule. These disulfide bonds play an important role in stabilization of an amphipathic three-dimensional structure that imparts activity similar to a surfactant in the hydrophobin, which enables the hydrophobin to be self-assembled into an amphipathic monolayer at a hydrophilic-hydrophobic interface. Hydrophobin is classified into Class I and Class II depending on a hydropathy plot, solubility, and a structure formed during self-assembly. Both Class I and Class II hydrophobins form an amphipathic monolayer at a hydrophilic-hydrophobic interface; however, Class I hydrophobin forms amyloid-like rodlets which are insoluble at a hydrophilic-hydrophobic interface, whereas, Class II hydrophobin forms a monolayer having a high solubility at a hydrophilic-hydrophobic interface.

Due to the above features, hydrophobin has been spotlighted in the biomaterial industry. Accordingly, the use of hydrophobin in cosmetics or food and beverage requiring stable and uniform foam has been actively studied. In addition, hydrophobin has received increasing attention as a next-generation innovative material such as a medical coating agent or a functional particle for a nano-structure applied to a living body in various industries.

Until now, methods of producing hydrophobin using a bacterium, a plant cell, yeast, or the like have been attempted, in addition to a method using mold which is the original strain as it is. For example, a protein to be produced in a bacterium in an inclusion body form has been purified for use. However, current methods require a denaturation/refolding process to obtain a final hydrophobin protein, which means a significant increase in costs in the mass production of hydrophobin.

For example, it has been reported by BASF SE in 2009 that two recombinant Class I hydrophobins such as H*Protein A (yaaD-*A. nidulans* DewA-$His_6$) and H*Protein B (cleaved yaaD-*A. nidulans* DewA-$His_6$) are able to be produced to the extent of industrial applicability using a bacterium as a host; however, in this case, hydrophobin is also produced in an inclusion body form. Until now, there have been no reports of a case in which a recombinant hydrophobin is successfully expressed in a soluble form (Wendel et al. 2010).

In addition to the problem above, HPLC, two phase separation method (ATPS; aqueous two-phase systems) using a surfactant have been mainly used for purifying hydrophobin in the related art, but it takes a lot of time and cost during the purification due to a complex procedure and use of chemical materials that are not easy to handle. Therefore, these problems are required to be urgently solved.

RELATED ART DOCUMENT

Patent Document (Patent Document 1) Korean Patent Publication No. 1446054 (2014.09.24)
(Patent Document 2) Korean Patent Laid-Open Publication No. 2014-0022839

Non-Patent Document (Non-Patent Document 1) Bayry J. et al. PLOS Pathog 8(5):e1002700 (2012)
(Non-Patent Document 2) Linder M. B. et al. FEMS Microbiol Rev 29(5):877-896 (2005)
(Non-Patent Document 3) Kwan A H Y et al. PNAS USA 2006; 103:3621 LP 3626 (2006)
(Non-Patent Document 4) Wendel W. et al. Eur. Biophys. J. 39:457-468 (2010)

SUMMARY

An embodiment of the present disclosure is directed to providing a recombinant fusion protein for soluble expression of hydrophobin in a heterologous host, a method of producing the same, and a method of purifying soluble hydrophobin through the production method.

In one general aspect, a recombinant fusion protein expressed in a soluble form includes: a target protein; and a ramp tag for controlling a translation speed, fused at an N-terminal of the target protein, wherein a signal sequence of the N-terminal of the target protein is subjected to mutation including the deletion.

The target protein may be hydrophobin.

The target protein may be Class I hydrophobin.

The target protein may be DewA.

A wild type target protein may consist of an amino acid sequence of SEQ ID NO: 2.

The target protein may consist of an amino acid sequence of SEQ ID NO: 8 or 10.

The ramp tag may consist of an amino acid sequence of SEQ ID NO: 5.

The signal sequence may consist of a base sequence of SEQ ID NO: 3.

The mutation may be one or two or more selected from the group consisting of a substitution and a deletion of a part or all of amino acids of the signal sequence and an addition of a new amino acid.

In another general aspect, there is provided a base sequence encoding the recombinant fusion protein.

In still another general aspect, there is provided a vector for soluble expression of the recombinant fusion protein, the base sequence being introduced into the vector.

In still another general aspect, there is provided a transformant for soluble expression of the recombinant fusion protein, the transformant being transformed with the vector.

In still another general aspect, there is provided a method of purifying a recombinant fusion protein expressed in a soluble form, the method including: a) expressing a recombinant fusion protein in a soluble form by transforming a non-human host cell with a vector into which a base sequence encoding a recombinant fusion protein is introduced, the recombinant fusion protein including: a target protein; and a ramp tag for controlling a translation rate, fused at an N-terminal of the target protein; and b) purifying the expressed recombinant fusion protein.

Step b) above may include: b1) suspending the transformed cell and lysing and centrifuging the suspended cell to obtain a first supernatant; b2) shaking and then centrifuging a first mixture obtained by adding a first solvent to the first supernatant to obtain a second supernatant; and b3) shaking and then centrifuging a second mixture obtained by adding a second solvent to the second supernatant to recover the target protein.

The target protein may be hydrophobin.

The target protein may be Class I hydrophobin.

The target protein may be DewA.

A wild type target protein may consist of an amino acid sequence of SEQ ID NO: 2.

The target protein may consist of an amino acid sequence of SEQ ID NO: 8 or 10.

The ramp tag may be obtained by collecting a rare codon of the host cell.

The host cell may be a bacterium belonging to *Escherichia* sp., *Salmonellae* sp., *Yersinia* sp., *Shigella* sp., *Enterobacter* sp., *Pseudomonas* sp., *Proteus* sp., or *Klebsiella* sp.

Each of the first solvent and the second solvent may be selected from the group consisting of C3 organic solvents.

A volume ratio of the organic solvent to the first supernatant may be 1:2 or 1:3.

The ramp tag may consist of an amino acid sequence of SEQ ID NO: 5.

The rare codon may be collected by analyzing a frequency of the codon and the number of isoacceptor tRNA genes.

The frequency of the codon may be 0.1 to 1%. The number of isoacceptor tRNA genes may be 0 to 2.

The target protein may be a physiologically active protein including hormones and receptors thereof, biological response modifiers and receptors thereof, cytokines and receptors thereof, enzymes, antibodies, and antibody fragments.

In still another general aspect, there is provided a recombinant fusion protein expressed in a soluble form, the recombinant fusion protein being purified by the method.

Other features and aspects will be apparent from the following detailed description, the drawings, and the claims.

DETAILED DESCRIPTION

Hereinafter, a method of expressing hydrophobin in a soluble form and a method of purifying hydrophobin according to the present disclosure will be described in detail with reference to the accompanying drawings.

The drawings to be described below are provided by way of example so that the spirit of the present invention can be sufficiently transferred to those skilled in the art. Therefore, the present disclosure is not limited to the drawings suggested below but may be modified in many different forms. In addition, the drawings suggested below will be exaggerated in order to clarify the spirit of the present invention.

Technical terms and scientific terms used in the specification of the present disclosure have the general meanings understood by those skilled in the art to which the present disclosure pertains unless otherwise defined, and a description for the known function and configuration obscuring the present disclosure will be omitted in the following description and the accompanying drawings. In addition, singular forms used in the specification of the present disclosure may be intended to include plural forms unless otherwise specified. In addition, a unit used in the specification of the present disclosure unless otherwise specified is based on a weight. As an example, % or a unit of a ratio refers to wt % or a weight ratio.

The term "target protein" in the present disclosure is a protein intended to be produced in large quantities by those skilled in the art and refers to any protein that can be expressed in a transformant by inserting polynucleotide encoding the protein to a recombinant expression vector.

In addition, the term "recombinant protein" or "fusion protein" refers to a protein to which another protein is connected to an N-terminal or a C-terminal of an initial target protein sequence or refers to a protein to which another amino acid sequence is added. In addition, the above term refers to a recombinant fusion protein of the present disclosure obtained by linking a fusion partner to a target protein or refers to a recombinant protein of a target protein from which a fusion partner is removed by a protein cleaving enzyme.

The term "vector" or "expression vector" is a linear or circular DNA molecule consisting of fragments encoding polypeptide, the polypeptide consisting of elements and additional fragments provided for gene transcription and translation and being linked to the DNA molecule to be operable. The additional fragment includes a promoter and a transcription termination signal sequence. The vector or the expression vector includes one or more replication origins, one or more selection markers, and the like. In general, the vector or the expression vector is derived from plasmid or virus DNA or from both of them.

The expression "comprise(s)" is intended to be open-ended transitional phrase having an equivalent meaning to an expression such as "include(s)", "contain(s)", "have(has)", or "is (are) characterized", and does not exclude elements, materials, or steps, which are not further recited. In addition, the expression "substantially consist(s) of" means that one specific element, material, and step, which are not recited with a specific element, material, and step, may be present at an amount having no unacceptably significant influence on at least one basic and novel technical idea of the disclosure. In addition, the expression "consist(s) of" means the presence of only the defined element, material, and step.

The terms "sample" and "specimen" in the present disclosure refer to subjects for analysis and are interchangeably used throughout the specification.

Hereinafter, a recombinant fusion protein expressed in a soluble form according to the present disclosure will be described in detail.

The recombinant fusion protein expressed in a soluble form is a recombinant fusion protein including a target protein and a ramp tag for controlling a translation rate, fused at an N-terminal of the target protein. A signal sequence of the N-terminal of the target protein is subjected to mutation.

In the recombinant fusion protein expressed in a soluble form according to an exemplary embodiment of the present disclosure, the target protein may be hydrophobin, such as a Class I hydrophobin, or a Class I DewA, and a wild type target protein may consist of an amino acid sequence of SEQ ID NO: 2. According to an exemplary embodiment of the present disclosure, the target protein of which the N-terminal has the mutated signal sequence may have an amino acid sequence of SEQ ID NO: 8 or 10, but the scope of the present disclosure is not limited thereto.

In the recombinant fusion protein expressed in a soluble form according to an exemplary embodiment of the present disclosure, the ramp tag may be composed of 1 to 20 amino acids, preferably 6 to 12 amino acids, and more preferably 6 to 8 amino acids, but is not limited thereto. In the recombinant fusion protein according to an exemplary embodiment of the present disclosure, the ramp tag may consist of an amino acid sequence of SEQ ID NO: 5.

In the present disclosure, a ramp tag for controlling a translation rate for expressing a recombinant fusion protein, a method used for an application thereof, and the like is disclosed in Korean Patent Publication No. 1446054 registered by the present applicant, the contents of which are incorporated herein by reference in their entirety. In a case where the contents corresponding to the detailed description of the present disclosure are not particularly described, the method used in the above patent publication or a method appropriately modified to meet the object of the present disclosure, and the like may be applied.

As a specific example related to the content disclosed in Korean Patent Publication No. 1446054, a ramp tag for controlling a translation rate is prepared by using a method including: making a rare codon table according to a host cell; converting a DNA sequence of a target gene into codons; analyzing a frequency and position at which rare codons in the rare codon table appear in an open reading frame (ORF) of the target gene; and collecting and arranging the rare codons. Then, a protein that has a high added value but is difficult to be expressed, for example, esterase, β-glucosidase, cytolysin A, single chain Fv (scFv), asparaginase B, tetra-cell adhesion molecule (T-CAM), or B3(Fv)PE38, is effectively expressed by using the ramp tag.

In the present disclosure, the ramp tag may be prepared in a form in which the ramp tag for controlling a translation rate of the above patent publication is fused at the N-terminal of the target protein. By doing so, the ramp tag may be included in the recombinant fusion protein.

In the recombinant fusion protein expressed in a soluble form according to an exemplary embodiment of the present disclosure, the signal sequence may be confirmed by a general method such as SignalP (see SignalP 5.0 improves signal peptide predictions using deep neural networks. José Juan Almagro Armenteros, Konstantinos D. Tsirigos, Casper Kaae Sønderby, Thomas Nordahl Petersen, Ole Winther, Søren Brunak, Gunnar von Heijne and Henrik Nielsen. Nature Biotechnology, 37, 420-423 (2019)) which is an exocrine signal sequence prediction program, but the present disclosure is not limited thereto. According to an exemplary embodiment of the present disclosure, the signal sequence may consist of a base sequence of SEQ ID NO: 3.

In the recombinant fusion protein expressed in a soluble form according to an exemplary embodiment of the present disclosure, the mutation may be one or two or more selected from the group consisting of a substitution and a deletion of a part or all of amino acids of the signal sequence and an addition of a new amino acid.

According to an exemplary embodiment of the present disclosure, the mutation may be a deletion of a part or all of amino acids of the signal sequence, and for example, the $1^{st}$ amino acid to the $18^{th}$ amino acid of a sequence may be deleted. According to an exemplary embodiment of the present disclosure, as a specific example, the entire signal sequence corresponding to the underlined part of SEQ ID NO: 1 shown in Table 1, below, may be deleted, but the present disclosure is not limited thereto.

Figure 1:
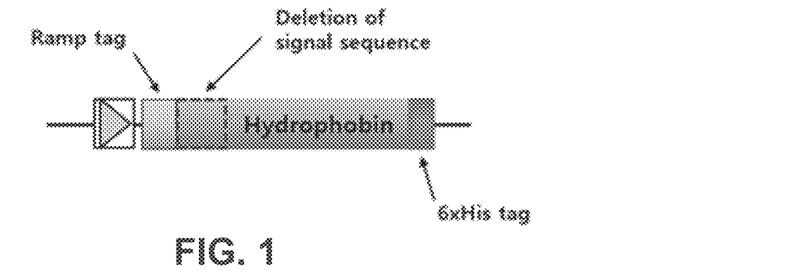
FIG. 1 is a schematic view of a structure of a recombinant fusion protein for soluble expression of hydrophobin.

According to an exemplary embodiment of the present disclosure, FIG. 1 illustrates an example of a structure of a recombinant fusion protein for soluble expression of a target protein. The ramp tag is fused at an N-terminal of the hydrophobin used as the target protein. The entire signal sequence of the hydrophobin is deleted. Various types of amino acid sequences that may be used for detecting and purifying a protein may be fused at a C-terminal of the hydrophobin used as the target protein, and for example, one or two or more tags or proteins selected from the group consisting of His tag, T7 tag, S-tag, Flag-tag, HA-tag, V5 epitope, PelB, and Xpress epitope may be used. In some embodiments, codons with respect to tags coded with six histidines (6×His tag) may be connected, but the present disclosure is not limited thereto.

From examples to be described below, it was newly confirmed that, in the case of the recombinant fusion protein expressed in a soluble form according to the present disclosure, a target protein expressed only in an insoluble inclusion body form in the related art is expressed in a soluble protein form. Accordingly, the present inventors solved the fundamental problem such as protein refolding, which was the existing problem, and confirmed that a target protein having the original activity may be obtained in a high yield. Further, the present inventors have established a process capable of purifying a target protein with a significantly simplified procedure and high separation yield as compared with a process of purifying the target protein in the insoluble inclusion body form according to the related art.

The present disclosure provides a base sequence encoding the recombinant fusion protein. According to an exemplary embodiment of the present disclosure, for example, the base sequence may have a base sequence of SEQ ID NO: 1.

In addition, the present disclosure provides a vector for soluble expression of the protein, the base sequence being introduced into the vector.

In addition, the present disclosure provides a transformant for soluble expression of the recombinant fusion protein, the transformant being transformed with the vector. According to an exemplary embodiment of the present disclosure, the type of the transformant is not particularly limited as long as it may achieve the object of the present disclosure. However, an individual facilitated for a gene expression, for example, *Escherichia coli* or the like may be used.

Hereinafter, a method of purifying a recombinant fusion protein expressed in a soluble form according to the present disclosure will be described in detail.

The method of purifying a recombinant fusion protein expressed in a soluble form according to the present disclosure includes: a) expressing a recombinant fusion protein in a soluble form by transforming a non-human host cell with a vector into which a base sequence encoding a recombinant fusion protein is introduced, the recombinant fusion protein including: a target protein; and a ramp tag for controlling a translation rate, fused at an N-terminal of the target protein; and b) purifying the expressed recombinant fusion protein.

In the method of purifying a recombinant fusion protein expressed in a soluble form according to the present disclosure, step b) above may include: b1) suspending the transformed cell and lysing and centrifuging the suspended cell to obtain a first supernatant; b2) shaking and then centrifuging a first mixture obtained by adding a first solvent to the first supernatant to obtain a second supernatant; and b3) shaking and then centrifuging a second mixture obtained by adding a second solvent to the second supernatant to recover the target protein.

In the method of purifying a recombinant fusion protein expressed in a soluble form according to an exemplary embodiment of the present disclosure, the target protein may consist of an amino acid sequence of SEQ ID NO: 2. According to an exemplary embodiment of the present disclosure, the target protein may be hydrophobin, such as a Class I hydrophobin, or a Class I DewA, but the scope of the present disclosure is not limited thereto.

In the method of purifying a recombinant fusion protein expressed in a soluble form according to an exemplary embodiment of the present disclosure, the ramp tag may be obtained by collecting a rare codon of the host cell, but is not limited thereto.

In the method of purifying a recombinant fusion protein expressed in a soluble form according to an exemplary embodiment of the present disclosure, the host cell may be a bacterium belonging to *Escherichia* sp., *Salmonellae* sp., *Yersinia* sp., *Shigella* sp., *Enterobacter* sp., *Pseudomonas* sp., *Proteus* sp., or *Klebsiella* sp, but is not limited thereto. According to an exemplary embodiment of the present disclosure, as a specific example, *Escherichia* sp. may be used, and more specifically, *E. coli* BL21 or the like may be used.

In the method of purifying a recombinant fusion protein expressed in a soluble form according to an exemplary embodiment of the present disclosure, a two phase separation method using an organic solvent may be used in the purification, but the present disclosure is not limited thereto. Any method may be appropriately introduced as long as it is a purification method capable of separating the soluble protein according to the present disclosure with high efficiency.

In a case where the organic solvent is used in the purification, each of the first solvent and the second solvent may be selected from the group consisting of $C_3$ organic solvents. Specific examples of the first solvent and the second solvent include isopropyl alcohol. In addition, according to an exemplary embodiment of the present disclosure, as a specific example, in a case where isopropyl alcohol is used as each of the first solvent and the second solvent and a two phase separation method is applied, a target protein expressed in a soluble form may be separated with high efficiency. However, the scope of the present disclosure is not limited thereto.

Figure 3:
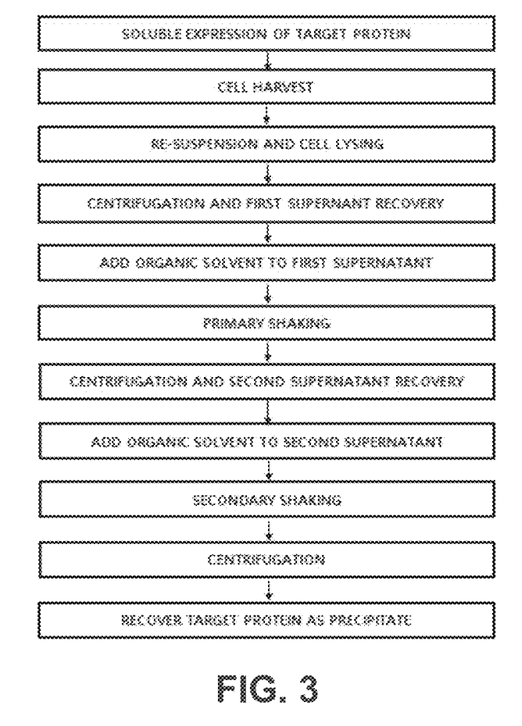
FIG. 3 illustrates an example of a flowchart of a process of purifying the soluble hydrophobin expressed according to the present disclosure.

The purification of the recombinant fusion protein expressed in a soluble form by the two-phase separation method according to the present disclosure is a new attempt that has not been applied in the related art (refer to Korean Patent Laid-Open Publication No. 2014-0022839, there have been attempts to purify hydrophobin using $C_1$-$C_3$ alcohol, but it was not a purification method for soluble expression). Thus, it was confirmed that a protein expressed in a soluble form may be separated and purified with high efficiency from specific examples to be described below. FIG. 3 illustrates an example of the method of purifying a recombinant fusion protein expressed in a soluble form by the two phase separation method using the organic solvent according to the present disclosure. In FIG. 3, it is confirmed that the protein expressed in a soluble form may be purified by the above method with high efficiency.

In the method of purifying a recombinant fusion protein expressed in a soluble form according to an exemplary embodiment of the present disclosure, processes such as recovery, suspension, and lysing of cells that are performed after the soluble expression of the target protein may be performed by appropriately introducing a reagent, method, and the like known to those skilled in the art in a range in which the object of the present disclosure may be achieved.

In the method of purifying a recombinant fusion protein expressed in a soluble form according to an exemplary embodiment of the present disclosure, the centrifugation in the sub-step b1) may be performed in a temperature range of 1 to 10° C., or 2 to 8° C., or 3 to 6° C. Since the first supernatant may be effectively separated from the lysed cell in the above range, the centrifugation may be performed in the above range.

In addition, the centrifugation in each of the sub-step b2) and b3) may be performed in a temperature range of 15 to 28° C., or 17 to 25° C., or 19 to 23° C. Since the second supernatant and the target protein may be effectively separated from the first mixture and the second mixture, respectively, in the above range, each centrifugation may be performed in the above range.

In the method of purifying a recombinant fusion protein expressed in a soluble form according to an exemplary embodiment of the present disclosure, the centrifugation may be performed at 3,000 to 20,000 rpm for 1 to 90 minutes. According to an exemplary embodiment of the present disclosure, the centrifugation in the sub-step b1) may be performed at 3,000 to 10,000 rpm, or 4,000 to 8,000 rpm, or 5,000 to 7,000 rpm, for 40 to 80 minutes, or 45 to 75 minutes, or 50 to 70 minutes, but is not limited thereto. Since the first supernatant may be effectively separated from the lysed cell in the above range, the centrifugation may be performed in the above range.

In addition, the centrifugation in the sub-step b2) may be performed at 6,000 to 15,000 rpm, or 7,500 to 13,500 rpm, or 8,500 to 11,500 rpm, for 40 to 80 minutes, or 45 to 75 minutes, or 50 to 70 minutes, but is not limited thereto. Since the second supernatant may be effectively separated from the first mixture in the above range, the centrifugation may be performed in the above range.

In addition, the centrifugation in the sub-step b3) may be performed at 6,000 to 15,000 rpm, or 7,500 to 13,500 rpm, or 8,500 to 11,500 rpm, for 1 to 20 minutes, or 4 to 16 minutes, or 7 to 13 minutes, but is not limited thereto. Since the target protein may be effectively separated from the second supernatant in the above range, the centrifugation may be performed in the above range.

In the method of purifying a recombinant fusion protein expressed in a soluble form according to an exemplary embodiment of the present disclosure, a volume ratio of the organic solvent to the first supernatant may be 1:1.5 or 1:4, or 1:2 or 1:3.5, or 1:2 or 1:3, but is not limited thereto. According to an exemplary embodiment of the present disclosure, as a specific example, the volume ratio thereof may be 1:2.5.

In addition, in the method of purifying a recombinant fusion protein expressed in a soluble form according to an exemplary embodiment of the present disclosure, a volume ratio of the organic solvent to the second supernatant may be 1:0.5 or 1:1.5, preferably 1:0.6 or 1:1.4, and more preferably 1:0.8 or 1:1.2, but is not limited thereto. According to an exemplary embodiment of the present disclosure, as a specific example, the volume ratio thereof may be 1:1.

In the method of purifying a recombinant fusion protein expressed in a soluble form according to an exemplary embodiment of the present disclosure, the target protein may be hydrophobin, such as a Class I hydrophobin, or a Class I DewA, and a wild type target protein may consist of an amino acid sequence of SEQ ID NO: 2. According to an exemplary embodiment of the present disclosure, the target protein of which the N-terminal has the mutated signal sequence may have an amino acid sequence of SEQ ID NO: 8 or 10, but the scope of the present disclosure is not limited thereto.

In the method of purifying a recombinant fusion protein expressed in a soluble form according to an exemplary embodiment of the present disclosure, the ramp tag may consist of 1 to 20 amino acids, preferably 6 to 12 amino acids, and more preferably 6 to 8 amino acids, but is not limited thereto. In the recombinant fusion protein according to an exemplary embodiment of the present disclosure, the ramp tag may consist of an amino acid sequence of SEQ ID NO: 5.

In the method of purifying a recombinant fusion protein expressed in a soluble form according to an exemplary embodiment of the present disclosure, the rare codon may be collected by analyzing a frequency of the codon and the number of isoacceptor tRNA genes.

In the method of purifying a recombinant fusion protein expressed in a soluble form according to an exemplary embodiment of the present disclosure, the frequency of the codon may be 0.05 to 3%, and preferably 0.1 to 1%, but is not limited thereto.

In the method of purifying a recombinant fusion protein expressed in a soluble form according to an exemplary embodiment of the present disclosure, the number of isoacceptor tRNA genes may be 0 to 2.

In the method of purifying a recombinant fusion protein expressed in a soluble form according to an exemplary embodiment of the present disclosure, the target protein may be a physiologically active protein including hormones and receptors thereof, biological response modifiers and receptors thereof, cytokines and receptors thereof, enzymes, antibodies, and antibody fragments.

In the method of purifying a recombinant fusion protein expressed in a soluble form according to an exemplary embodiment of the present disclosure, as a specific example, the target protein may be selected from the group consisting of hydrophobin, GST, MBP, NusA, CBP, GFP, Thioredoxin, Mistic, Sumo, and DSB, and more specifically, the target protein may be hydrophobin, but is not limited thereto.

Hereinafter, the present disclosure will be described in detail with reference to examples. The examples are provided only to explain the present disclosure in more detail, but the scope of the present disclosure is not limited by these examples.

Reagent, Material, and Protocol

Target protein: GenBank ID: gi67902037, Class I hydrophobin DewA (BASF, 2009) derived from *Aspergillus nidulans*, the target protein was synthesized by Bioneer Inc. (Daejeon, Korea) based on the genetic information provided by GenBank.

The ramp tag was prepared by the method of analyzing codon usage of *E. coli* described in Korean Patent Publication No. 1446054.

The pET24a plasmid vector was obtained from New England Labs (UK).

Other reagents were obtained from Sigma Aldrich (US).

Experimental Example 1

Gene Manipulation for Recombinant Fusion Protein Expression

In order to confirm soluble expression of a target protein expressed in an insoluble inclusion body form in the related art, Class I hydrophobin DewA derived from *A. nidulans* was used as a target protein. A base sequence and an amino acid sequence thereof are shown in Table 1.

TABLE 1

Base Sequence and Amino Acid Sequence
of Class 1 Hydrophobin DewA

| SEQ ID NO: | Classification | Sequence (5' → 3') |
|---|---|---|
| 1 | Base sequence of DewA | atgcgcttcatcgtctct ctcctcgccttcactgcc gcggccaccgcaaccgcc ctcccggcctctgccgca aagaacgcgaagctggcc acctcggcggccttcgcc aagcaggctgaaggcacc acctgcaatgtcggctcg |

TABLE 1-continued

Base Sequence and Amino Acid Sequence of Class 1 Hydrophobin DewA

| SEQ ID NO: | Classification | Sequence (5' → 3') |
|---|---|---|
|  |  | atcgcttgctgcaactcc cccgctgagaccaacaac gacagtctgttgagcggt ctgctcggtgctggctt ctcaacgggctctcgggc aacactggcagcgcctgc gccaaggcgagcttgatt gaccagctgggtctgctc gctctcgtcgaccacact gaggaaggccccgtctgc aagaacatcgtcgcttgc tgccctgagggaaccacc aactgtgttgccgtcgac aacgctggcgccggtacc aaggctgagtaa |
| 2 | Amino acid sequence of DewA | MRFIVSLLAFTAAATATA LPASAAKNAKLATSAAFA KQAEGTTCNVGSIACCNS PAETNNDSLLSGLLGAGL LNGLSGNTGSACAKASLI DQLGLLALVDHTEEGPVC KNIVACCPEGTTNCVAVD NAGAGTKAE |
| 3 | Signal sequence of DewA (entire base sequence)[a] | atgcgcttcatcgtctct cctctcgccttcactgcc gcggccaccgcaaccgcc ctcccggcctctgccgca |

[a]The signal sequence is a sequence predicted by using SignalP (Ver 4.0) which is an exocrine signal sequence prediction program.

A part or all of the signal sequence was deleted by using a general polymerase chain reaction (PCR) method well known to those skilled in the art.

In addition, a sequence of a ramp tag linked to an N-terminal of the Class I hydrophobin DewA used as the target protein was produced by applying the method of analyzing a rare codon disclosed in Korean Patent Publication No. 1446054. A base sequence and an amino acid sequence thereof are shown in Table 2.

TABLE 2

Base Sequence and Amino Acid Sequence of Ramp Tag, and Base Sequence of His-Tag

| SEQ ID NO: | Classification | Sequence (5' → 3') |
|---|---|---|
| 4 | Base sequence of ramp tag | cttcacagt cctaatccc |
| 5 | Amino acid sequence of ramp tag | LPASAA |
| 6 | Base sequence of 6 x His Tag | caccaccac caccaccac |

An experimental group in which a part or all of the signal sequence in the base sequence of the Class I hydrophobin DewA of Table 1 was deleted was prepared, and then sequences of hydrophobin DewA of which a signal sequence was mutated were given from SEQ ID NO 7 as shown in Table 3.

TABLE 3

Mutated Hydrophobin DewA according to Signal Sequence Mutation

| SEQ ID NO: | Experimental group | Base sequence and amino acid sequence of mutated hydrophobin (5' → 3') |
|---|---|---|
| 7 | Example 1 | aagaacgcgaagctg gccacctcggcggcc ttcgccaagcaggct gaaggcaccacctgc aatgtcggctcgatc gcttgctgcaactcc cccgctgagaccaac aacgacagtctgttg agcggtctgctcggt gctgccttctcaac gggctctcgggcaac actggcagcgcctgc gccaaggcgagcttg attgaccagctgggt ctgctcgctctcgtc gaccacactgaggaa ggccccgtctgcaag aacatcgtcgcttgc tgccctgagggaacc accaactgtgttgcc gtcgacaacgctggc gccggtaccaaggct gagtaa |
| 8 |  | KNAKLATSAAFAKQA EGTTCNVGSIACCNS PAETNNDSLLSGLLG AGLLNGLSGNTGSAC AKASLIDQLGLLALV DHTEEGPVCKNIVAC CPEGTTNCVAVDNAG AGTKAE |
| 9 | Example 2 | ctcccggcctctgcc gcaaagaacgcgaag ctggccacctcggcg gccttcgccaagcag gctgaaggcaccacc tgcaatgtcggctcg atcgcttgctgcaac tcccccgctgagacc aacaacgacagtctg ttgagcggtctgctc ggtgctggccttctc aacgggctctcgggc aacactggcagcgcc tgcgccaaggcgagc ttgattgaccagctg ggtctgctcgctctc gtcgaccacactgag gaaggccccgtctgc aagaacatcgtcgct tgctgccctgaggga accaccaactgtgtt gccgtcgacaacgct ggcgccggtaccaag gctgagtaa |
| 10 |  | LPASAAKNAKLATSA AFAKQAEGTTCNVGS IACCNSPAETNNDSL LSGLLGAGLLNGLSG NTGSACAKASLIDQL GLLALVDHTEEGPVC KNIVACCPEGTTNCV AVDNAGAGTKAE |
| 1 | Comparative Example 1 | atgcgcttcatcgtc tctcctcgccttc actgccgcggccacc gcaaccgccctcccg gcctctgccgcaaag |

TABLE 3-continued

Mutated Hydrophobin DewA according to Signal Sequence Mutation

| SEQ ID NO: | Experimental group | Base sequence and amino acid sequence of mutated hydrophobin (5' → 3') |
|---|---|---|
| | | aacgcgaagctggcc<br>acctcggcggccttc<br>gccaagcaggctgaa<br>ggcaccacctgcaat<br>gtcggctcgatcgct<br>tgctgcaactccccc<br>gctgagaccaacaac<br>gacagtctgttgagc<br>ggtctgctcggtgct<br>ggccttctcaacggg<br>ctctcgggcaacact<br>ggcagcgcctgcgcc<br>aaggcgagcttgatt<br>gaccagctgggtctg<br>ctcgctctcgtcgac<br>cacactgaggaaggc<br>cccgtctgcaagaac<br>atcgtcgcttgctgc<br>cctgagggaaccacc<br>aactgtgttgccgtc<br>gacaacgctggcgcc<br>ggtaccaaggctgag<br>taa |

Example 1

The base sequence of SEQ ID NO: 7 obtained by deleting the entire signal sequence in the base sequence of SEQ ID NO: 1, the base sequence of SEQ ID: 4 of the ramp tag, and the sequence of SEQ ID NO: 6 of 6×His Tag were synthesized as in the order illustrated in the schematic view of FIG. 1, and then the pET24a plasmid vector was used by a general cloning method, thereby preparing a recombinant expression vector (pET24a-Ramp-DewA(-ss)-6×His).

Example 2

A recombinant expression vector was prepared in the same procedure and condition as those of Example 1, except that the base sequence of the mutated hydrophobin was changed to a base sequence of SEQ ID NO: 8.

Comparative Example 1

A recombinant expression vector (pET24a-Ramp-DewA-6×His) was prepared in the same procedure and condition as those of Example 1, except that the signal sequence (SEQ ID NO: 1) was not mutated.

Experimental Example 2

Confirmation of Soluble Expression of Recombinant Fusion Protein

In order to confirm soluble expression of the recombinant fusion protein in each experimental group of Table 3, *E. coli* BL21(DE3) was transformed with each recombinant expression vector, and the transformed *E. coli* BL21(DE3) was inoculated into a solid LB medium (10 g/L of NaCl, 10 g/L of tryptone, 5 g/L of yeast extract) containing agar to which 100 ug/mL of kanamycin was added and then cultured in a solid state at 37° C. for 12 hours.

Thereafter, in each experimental group, three single colonies (#1, #2, and #3) were inoculated into each of 3.5 mL of a liquid LB medium and then pre-cultured at 37° C. and 220 rpm for 5 or 6 hours.

100 uL of the pre-cultured medium was sub-cultured in 3.5 mL of a new LB medium in which 100 ug/mL of kanamycin was added and cultured at 37° C. and 220 rpm, and then, when an absorbance ($OD_{600}$) at 600 nm has reached about 0.7, 0.2 mM isopropyl β-D-thiogalactopyranoside (IPTG) was added to induce expression of protein.

After the addition of IPTG, each experimental group was separated into two temperature experimental groups of 37° C. and 18° C., and the expression of the Class I hydrophobin DewA used as the target protein was induced at each temperature and 250 rpm for 3 hours.

Thereafter, the target protein expressed by the following method was recovered from the *E. coli* cultured at each temperature.

a) 3.5 mL of each culture medium was centrifuged at 4° C. and 13,200 rpm for 2 minutes to obtain a precipitate, and the precipitate was suspended in 200 mM Tris-HCl (pH 8.0) and then lysed by ultrasonic waves using a pulse of 2 seconds for 20 seconds.

b) The recovered cell lysate was centrifuged at 4° C. and 13,200 rpm for 20 minutes, thereby obtaining a first supernatant from which cell debris was removed. In this case, after the cell lysing, an analysis sample for SDS-PAGE analysis (total fraction: T) was obtained, and after the centrifugation of the cell lysate, an analysis sample (soluble fraction: S) was also obtained to perform the SDS-PAGE analysis. A residual fraction after the centrifugation indicates an insoluble fraction I, and the results thereof are illustrated in FIGS. 2A and 2B.

Figure 2A:
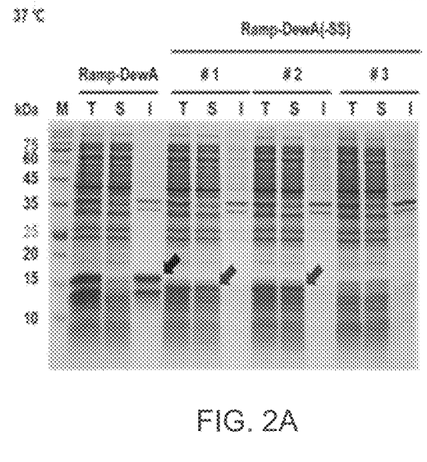
FIGS. 2A and 2B show SDS-PAGE analysis results after culturing at (a) 37° C. and (b) 18° C. to confirm soluble expression of hydrophobin.
Figure 2B:
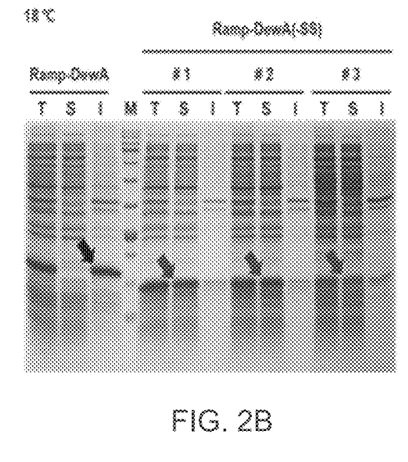

It was confirmed from the results of FIGS. 2A and 2B that, in Comparative Example 1, when the expression was induced through IPTG and then the protein was expressed at 37° C., the expression amount (95 wt %) of the target protein DewA in the insoluble fraction I was significantly larger than that in the soluble fraction S (5 wt %).

On the other hand, it was confirmed that, in Example 1, the expression amount (7 wt %) of the target protein DewA in the insoluble fraction I was significantly reduced as compared in the soluble fraction S (93 wt %), and thus, most of the DewA protein was expressed in a soluble form.

The above results mean that the Class I hydrophobin DewA used as the target protein of the present disclosure was expressed in a soluble form with high efficiency by the preparation of the recombinant fusion protein according to the present disclosure. In addition, it was confirmed that since high expression of 15% or more of a total protein of the *E. coli* may be exhibited, when a high cell density culture was performed, 1 g/L of a soluble protein may be produced.

In addition, it was confirmed that in Comparative Example 1, when the culture was performed at 18° C., the expression amount (to 100 wt %) of the target protein DewA in the insoluble fraction I was mostly occupied as compared in the soluble fraction S (hardly occupied).

On the other hand, it was confirmed that in Example 1, the expression amount (5 wt %) of the target protein DewA in the insoluble fraction I was significantly reduced as compared in the soluble fraction S (95 wt %), and thus, most of the DewA protein was expressed in a soluble form.

This is similar to the culture at 37° C., and it could be confirmed that the target protein was expressed in a soluble form by deletion of the signal sequence and fusion of the ramp tag in the recombinant fusion protein, regardless of the culture temperature.

Meanwhile, it was confirmed that in Example 2, the soluble expression of the target protein DewA was somewhat improved as compared with Comparative Example 1. However, it was evaluated that it was not applicable to the purification method of the present disclosure premised on the soluble expression of the target protein (data not shown).

It should be understood that it is obvious to those skilled in the art that the above results were shown by way of example only for the Class I hydrophobin DewA; however, the above results can be reasonably generalized by being extended to at least Class I hydrophobin and broadly to the whole hydrophobin, because hydrophobin has a common feature to form amphipathic structure with four disulfide bonds (S—S) in a molecule due to eight cysteines included in the molecule.

Experimental Example 3

Purification of Class I Hydrophobin DewA Expressed in Soluble Form

In each experimental group of Experimental Example 1, a recombinant fusion protein was expressed in *E. coli* in the same manner as that of Experimental Example 2, and then Class I hydrophobin DewA used as the target protein expressed in a soluble form was purified by the following purification process:

a) The Class I hydrophobin DewA was expressed in the same manner as that in each experimental group of Table 3.
b) A culture medium in which DewA was expressed was centrifuged at 4° C. and 6,000 rpm to recover cells.
c) The recovered cells were re-suspended with 200 mM Tris-HCl (pH 8.0) and were sonicated to lyse the cells. In this case, the entire fraction sample was obtained.
d) The lysed cells were centrifuged at 4° C. and 10,000 rpm for 1 hour to recover a first supernatant. In this case, a soluble fraction sample was obtained.
e) Isopropyl alcohol whose volume is greater by 2.5 times than that of the first supernatant was slowly added to the first supernatant to obtain a first mixture.
f) The first mixture was shaken at 30° C. and 200 to 250 rpm for 15 minutes.
g) After the shaking, the first mixture was centrifuged at 20° C. (room temperature) and 10,000 rpm for 10 minutes to recover a second supernatant.
h) Isopropyl alcohol whose volume is the same as that of the second supernatant was slowly added to the second supernatant to obtain a second mixture.
i) The second mixture was shaken at 30° C. and 200 to 250 rpm for 15 minutes.
j) Thereafter, after the shaking, the second mixture was centrifuged at 20° C. (room temperature) and 10,000 rpm for 10 minutes to separate Class I hydrophobin DewA protein used as the target protein purified in a white precipitated form.

Each of the total fraction sample and the soluble fraction samples obtained in c) and d) and the target protein DewA in the white precipitated form obtained in j) was dissolved in 1 mL of 200 mM Tris-HCl (pH 8.0) used as a re-suspension solvent, 1 mL of Tris-HCl was continuously and sequentially added, and then SDS-PAGE analysis of the diluted sample was performed. The results thereof are illustrated in FIG. 4.

Figure 4:
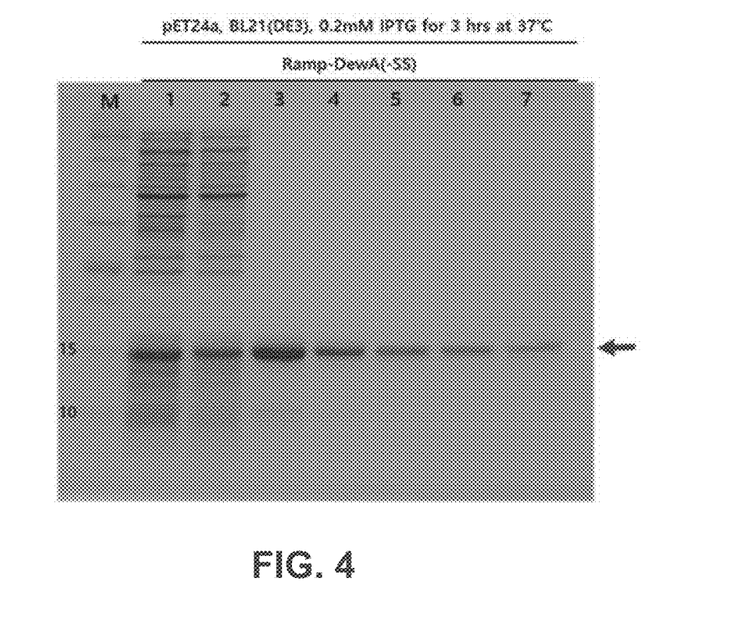
FIG. 4 shows an SDS-PAGE analysis result for confirming purification efficiency of the soluble hydrophobin purified according to the present disclosure.

In FIG. 4, lane 1 represents an total fraction sample T, lane 2 represents a soluble fraction sample S, lane 3 represents a sample obtained by dissolving Class I hydrophobin DewA used as a target protein purified by the purification method in 1 mL of 200 mM Tris-HCl (pH 8.0), lane 4 represents a sample obtained by additionally adding 1 mL of Tris-HCl to the sample of lane 3, and each of lanes 5 to 7 represents a diluted sample obtained by adding 1 mL of 200 mM Tris-HCl to the previous sample in the same manner as described above.

As can be seen from the above results, it is shown that 80% or more of the total fraction sample of lane 1 is also observed in the soluble fraction sample of lane 2, and, in each of lanes 3 to 7, the target protein expressed in a soluble form may be efficiently purified by the two phase separation method using the organic solvent of the present disclosure.

It was confirmed from the results that the hydrophobin expressed in a soluble form was efficiently purified by a simple purification method without a complex physical and chemical purification process.

In addition, it should be understood that it is obvious to those skilled in the art that, similarly to Experimental Example 2, the above results were shown by way of example only for the Class I hydrophobin DewA; however, the above results can be reasonably generalized by being extended to at least Class I hydrophobin and broadly to the whole hydrophobin, because hydrophobin has a common feature to form amphipathic structure with four disulfide bonds (S—S) in a molecule due to eight cysteines included in the molecule.

Comparative Example 2

The recombinant fusion protein expressed through Example 1 was purified in the same procedure and condition as those of Experimental Example 3, except that each of methanol, ethanol, and isobutyl alcohol was used as the organic solvent instead of the isopropyl alcohol.

Comparative Example 3

The recombinant fusion protein expressed through Example 1 was purified in the same procedure and condition as those of Experimental Example 3, except that the amount of isopropyl alcohol to be mixed with the second supernatant was set to be the same as the volume of the first supernatant.

Comparative Example 4

The recombinant fusion protein expressed through Example 1 was purified in the same procedure and condition as those of Experimental Example 3, except that a concentration of the Tris-HCl (pH 8.0) used as a re-suspension solvent was set to be 50 mM and 400 mM.

As a result, it was confirmed that, when the purification was performed by a method outside the scope of the present disclosure in each of Comparative Examples 2 to 4, the Class I hydrophobin DewA expressed in a soluble form was not efficiently purified (data not shown).

Therefore, it should be understood that it is obvious to those skilled in the art that the hydrophobin expressed in a soluble form may be efficiently purified only by performing the purification under the purification process of the present disclosure and the corresponding condition, and as described in Experimental Examples 2 and 3, the above results were shown by way of example only for the Class I hydrophobin DewA; however, the above results can be reasonably generalized by being extended to at least Class I hydrophobin and broadly to the whole hydrophobin, because hydrophobin has a common feature to form amphipathic structure with four disulfide bonds (S—S) in a molecule due to eight cysteines included in the molecule.

Comparative Example 5

Purification of Hydrophobin According to Related Art (Triton X-114 Used as Nonionic Surfactant)

A fusion protein was purified using Triton X-114 used as a nonionic surfactant by a method described in the document (Clifton N. J. et al. Article in Methods in molecular biology, 2012) including the corresponding contents.

The recombinant expression vector (pET24a-Ramp-DewA(-ss)-6×His) of Example 1 was cultured at 37° C. and 200 rpm and 0.2 mM IPTG was added at the time at which an absorbance at 600 nm has reached about 0.5 to induce expression of the recombinant fusion protein.

The expressed cells were centrifuged at 10,000 rpm to separate the medium and the cells from each other, and the recovered cells were sonicated, thereby obtaining a total fraction sample.

The total fraction sample was centrifuged at 4° C. and 10,000 rpm for 30 minutes to obtain a soluble fraction sample (supernatant).

Then, Triton X-114 used as a nonionic surfactant was added thereto in an amount of 5% of a total volume and mixed with the supernatant for 1 minute, and then the mixture was allowed to stand at room temperature to induce phase separation.

Then, only a lower part containing the hydrophobin was left by removing an upper part, isobutyl alcohol whose volume is the same as that of the lower part was added to the lower part, vortexing was performed for 1 minute to mix them, and the mixture was centrifuged at 4° C. and 5,000 rpm while confirming phase separation.

The upper part removed in the previous step was also extracted by using isobutyl alcohol in the same manner as described above.

Figure 5:
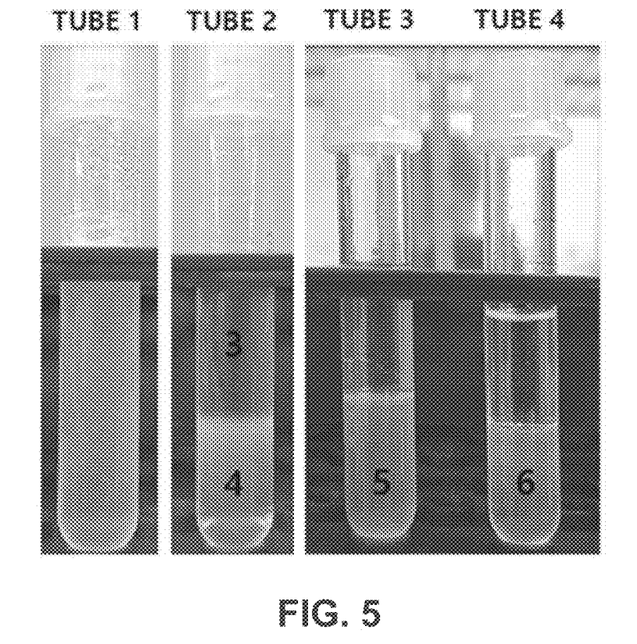
FIG. 5 illustrates a purification procedure of hydrophobin by a two phase separation method using Triton X-114 known in the related art.

The above procedure and results are illustrated in FIG. 5.

In FIG. 5, a tube 1 shows a state immediately after the cells are lysed, a total fraction sample 1 and a soluble fraction sample 2 after centrifugation of the total fraction sample 1 are obtained, a soluble fraction sample (supernatant) is mixed with Triton X-114, and then the mixture is subjected to vortexing.

A tube 2 shows a state after a phase is separated into an upper part 3 and a lower part 4.

A tube 3 shows a state after the upper part 3 is mixed with isobutyl alcohol and a phase of the mixture is separated into an upper part and a lower part 5. A tube 4 shows a state after the lower part 4 is mixed with isobutyl alcohol and a phase of the mixture is separated into an upper part and a lower part 6.

Figure 6A:
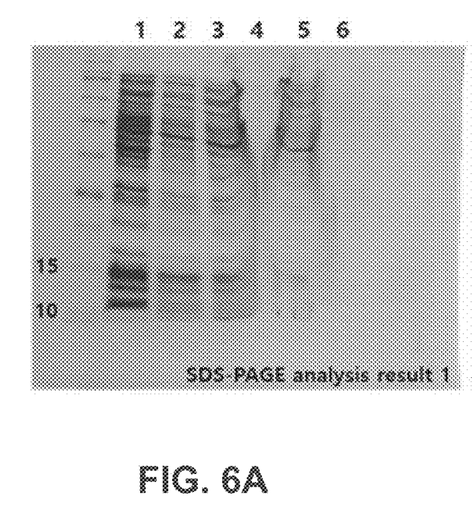
FIGS. 6A and 6B shows SDS-PAGE analysis results for confirming purification efficiency of the hydrophobin purified by the two phase separation method using the Triton X-114.
Figure 6B:
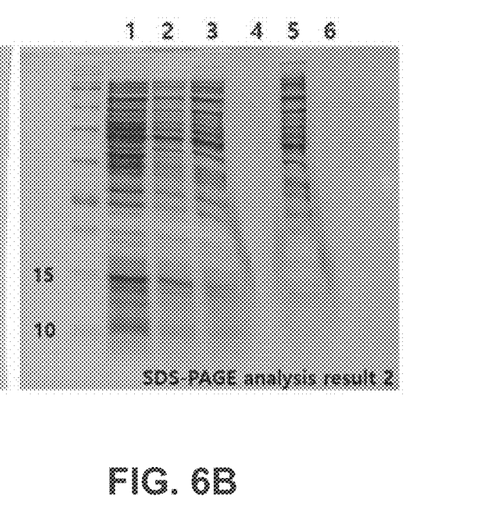

Results of performing two times of SDS-PAGE analysis on a total of six samples obtained in each step are illustrated in FIGS. 6A and 6B.

In FIGS. 6A and 6B, lane 1 represents a total fraction sample, lane 2 represents a soluble fraction sample, lane 3 represents a sample of the upper part in the tube 2, lane 4 represents a sample of the lower part in the tube 2, lane 5 represents a sample of the lower part in the tube 3, and lane 6 represents a sample of the lower part in the tube 4.

As described above, hydrophobin expressed in a soluble form to be expected in lane 6 was not observed, and the reason was that expression and purification of soluble hydrophobin were not performed by the purification method using Triton X-114 used as a nonionic surfactant according to the related art. However, it was confirmed that hydrophobin protein expressed in an insoluble inclusion body form in the related art was expressed in a soluble form, and then the hydrophobin protein was purified with high efficiency through a simple process by the configuration of the recombinant fusion protein and the purification method according to the present disclosure.

As set forth above, soluble expression and its simple purification of hydrophobin expressed in an inclusion body form in the related art is achieved by the soluble expression and the purification method according to the present disclosure, such that protein refolding in the related art is not required, thereby easily purifying and obtaining hydrophobin expressed in a soluble form with high efficiency.

The invention claimed is:

1. A method of purifying a recombinant fusion protein expressed in a soluble form, the method comprising:
   a) expressing the recombinant fusion protein in soluble form by transforming a bacterial host cell with a vector into which a base sequence encoding the recombinant fusion protein is introduced to form a transformed cell, the recombinant fusion protein including: a target protein; and a ramp tag for controlling a translation speed and tRNA recruiting, fused at an N-terminal of the target protein; and
   b) purifying the expressed recombinant fusion protein, wherein the target protein is hydrophobin, wherein b) includes:
      b1) suspending the transformed cell to form a suspended cell and lysing and centrifuging the suspended cell to obtain a first supernatant;
      b2) shaking and then centrifuging a first mixture obtained by adding a first solvent to the first supernatant to obtain a second supernatant; and
      b3) shaking and then centrifuging a second mixture obtained by adding a second solvent to the second supernatant to recover the target protein, wherein each of the first solvent and the second solvent is isopropyl alcohol, and wherein a volume ratio of the isopropyl alcohol to the first supernatant and second supernatant is 1:2 to 1:3, respectively, wherein the target protein is DewA.

2. The method of claim 1, wherein the target protein consists of an amino acid sequence of SEQ ID NO: 8 or 10.

3. The method of claim 1, wherein the bacterial host cell is a bacterium belonging to *Escherichia* sp., *Salmonellae* sp., *Yersinia* sp., *Shigella* sp., *Enterobacter* sp., *Pseudomonas* sp., *Proteus* sp., or *Klebsiella* sp.

4. The method of claim 1, wherein the ramp tag consists of an amino acid sequence of SEQ ID NO: 5.

* * * * *

SEQUENCE LISTING

```
Sequence total quantity: 10
SEQ ID NO: 1           moltype = DNA  length = 408
FEATURE                Location/Qualifiers
misc_feature           1..408
                       note = DewA nucleotide
source                 1..408
                       mol_type = other DNA
                       organism = synthetic construct
SEQUENCE: 1
atgcgcttca tcgtctctct cctcgccttc actgccgcgg ccaccgcaac cgccctcccg   60
gcctctgccg caaagaacgc gaagctggcc acctcggcgg ccttcgccaa gcaggctgaa  120
ggcaccacct gcaatgtcgg ctcgatcgct tgctgcaact ccccgctga gaccaacaac  180
gacagtctgt tgagcggtct gctcggtgct ggccttctca acgggctctc gggcaacact  240
ggcagcgcct gcgccaaggc gagcttgatt gaccagctgg gtctgctcgc tctcgtcgac  300
cacactgagg aaggccccgt ctgcaagaac atcgtcgctt gctgccctga gggaaccacc  360
aactgtgttg ccgtcgacaa cgctggcgcc ggtaccaagg ctgagtaa               408

SEQ ID NO: 2           moltype = AA  length = 135
FEATURE                Location/Qualifiers
REGION                 1..135
                       note = DewA amino acid
source                 1..135
                       mol_type = protein
                       organism = synthetic construct
SEQUENCE: 2
```

-continued

```
MRFIVSLLAF TAAATATALP ASAAKNAKLA TSAAFAKQAE GTTCNVGSIA CCNSPAETNN    60
DSLLSGLLGA GLLNGLSGNT GSACAKASLI DQLGLLALVD HTEEGPVCKN IVACCPEGTT   120
NCVAVDNAGA GTKAE                                                    135

SEQ ID NO: 3            moltype = DNA  length = 72
FEATURE                 Location/Qualifiers
misc_feature            1..72
                        note = DewA signal sequence
source                  1..72
                        mol_type = other DNA
                        organism = synthetic construct
SEQUENCE: 3
atgcgcttca tcgtctctct cctcgccttc actgccgcgg ccaccgcaac cgccctcccg    60
gcctctgccg ca                                                       72

SEQ ID NO: 4            moltype = DNA  length = 18
FEATURE                 Location/Qualifiers
misc_feature            1..18
                        note = Ramp Tag nucleotide
source                  1..18
                        mol_type = other DNA
                        organism = synthetic construct
SEQUENCE: 4
cttcacagtc ctaatccc                                                 18

SEQ ID NO: 5            moltype = AA  length = 6
FEATURE                 Location/Qualifiers
REGION                  1..6
                        note = Ramp Tag amino acid
source                  1..6
                        mol_type = protein
                        organism = synthetic construct
SEQUENCE: 5
LPASAA                                                               6

SEQ ID NO: 6            moltype = DNA  length = 18
FEATURE                 Location/Qualifiers
misc_feature            1..18
                        note = 6 x His Tag nucleotide
source                  1..18
                        mol_type = other DNA
                        organism = synthetic construct
SEQUENCE: 6
caccaccacc accaccac                                                 18

SEQ ID NO: 7            moltype = DNA  length = 336
FEATURE                 Location/Qualifiers
misc_feature            1..336
                        note = DewA nucleotide - Example 1
source                  1..336
                        mol_type = other DNA
                        organism = synthetic construct
SEQUENCE: 7
aagaacgcga agctggccac ctcggcggcc ttcgccaagc aggctgaagg caccacctgc    60
aatgtcggct cgatcgcttg ctgcaactcc cccgctgaga ccaacaacga cagtctgttg   120
agcggtctgc tcggtgctgg ccttctcaac gggctctcgg gcaacactgg cagcgcctgc   180
gccaaggcga gcttgattga ccagctgggt ctgctcgctc tcgtcgacca cactgaggaa   240
ggccccgtct gcaagaacat cgtcgcttgc tgccctgagg gaaccaccaa ctgtgttgcc   300
gtcgacaacg ctggcgccgg taccaaggct gagtaa                             336

SEQ ID NO: 8            moltype = AA  length = 111
FEATURE                 Location/Qualifiers
REGION                  1..111
                        note = DewA amino acid - Example 1
source                  1..111
                        mol_type = protein
                        organism = synthetic construct
SEQUENCE: 8
KNAKLATSAA FAKQAEGTTC NVGSIACCNS PAETNNDSLL SGLLGAGLLN GLSGNTGSAC    60
AKASLIDQLG LLALVDHTEE GPVCKNIVAC CPEGTTNCVA VDNAGAGTKA E            111

SEQ ID NO: 9            moltype = DNA  length = 354
FEATURE                 Location/Qualifiers
misc_feature            1..354
                        note = DewA nucleotide - Example 2
source                  1..354
                        mol_type = other DNA
                        organism = synthetic construct
SEQUENCE: 9
```

```
ctcccggcct ctgccgcaaa gaacgcgaag ctggccacct cggcggcctt cgccaagcag    60
gctgaaggca ccacctgcaa tgtcggctcg atcgcttgct gcaactcccc cgctgagacc   120
aacaacgaca gtctgttgag cggtctgctc ggtgctggcc ttctcaacgg gctctcgggc   180
aacactggca gcgcctgcgc caaggcgagc ttgattgacc agctgggtct gctcgctctc   240
gtcgaccaca ctgaggaagg ccccgtctgc aagaacatcg tcgcttgctg ccctgaggga   300
accaccaact gtgttgccgt cgacaacgct ggcgccggta ccaaggctga gtaa         354

SEQ ID NO: 10           moltype = AA  length = 117
FEATURE                 Location/Qualifiers
REGION                  1..117
                        note = DewA amino acid - Example 2
source                  1..117
                        mol_type = protein
                        organism = synthetic construct
SEQUENCE: 10
LPASAAKNAK LATSAAFAKQ AEGTTCNVGS IACCNSPAET NNDSLLSGLL GAGLLNGLSG    60
NTGSACAKAS LIDQLGLLAL VDHTEEGPVC KNIVACCPEG TTNCVAVDNA GAGTKAE      117
```